(12) United States Patent
Wajid

(10) Patent No.: US 8,438,924 B2
(45) Date of Patent: May 14, 2013

(54) METHOD OF DETERMINING MULTILAYER THIN FILM DEPOSITION ON A PIEZOELECTRIC CRYSTAL

(75) Inventor: Abdul Wajid, East Syracuse, NY (US)

(73) Assignee: Inficon, Inc., East Syracuse, NY (US)

( * ) Notice: Subject to any disclaimer, the term of this patent is extended or adjusted under 35 U.S.C. 154(b) by 350 days.

(21) Appl. No.: 13/020,381

(22) Filed: Feb. 3, 2011

(65) Prior Publication Data

US 2012/0201954 A1  Aug. 9, 2012

(51) Int. Cl.
*G01N 29/00* (2006.01)
(52) U.S. Cl.
USPC .................. 73/579; 73/589; 73/599
(58) Field of Classification Search .......... 73/579, 73/599

See application file for complete search history.

(56) References Cited

U.S. PATENT DOCUMENTS

| | | | |
|---|---|---|---|
| 5,112,642 A * | 5/1992 | Wajid | 427/10 |
| 5,869,763 A | 2/1999 | Vig et al. | |
| 5,873,154 A | 2/1999 | Ylilammi et al. | |
| 5,936,150 A * | 8/1999 | Kobrin et al. | 73/24.06 |
| 7,579,761 B2 * | 8/2009 | Nishihara et al. | 310/364 |
| 7,750,292 B2 | 7/2010 | Finlay | |
| 2002/0152803 A1 | 10/2002 | Larson, III et al. | |
| 2007/0278401 A1 | 12/2007 | Finlay | |
| 2008/0179995 A1 * | 7/2008 | Umeda et al. | 310/324 |
| 2009/0028526 A1 * | 1/2009 | Kuroda | 386/95 |
| 2009/0301169 A1 | 12/2009 | Higgins et al. | |
| 2010/0134210 A1 * | 6/2010 | Umeda | 333/189 |
| 2011/0298564 A1 * | 12/2011 | Iwashita et al. | 333/187 |

FOREIGN PATENT DOCUMENTS

WO  WO 2007/140943 A1  12/2007

OTHER PUBLICATIONS

International Search Report/Written Opinion (ISR/WO); Oct. 4, 2012; 7 pages.
Improving the accuracy of a quartz crystal microbalance with automatic determination of acoustic impedance ratio; Abdul Wajid; Rev. Sci. Instrum. 62 (8), © 1991 American Institute of Physics; pp. 2026-2033.
Investigation of film-thickness determination by oscillating quartz resonators with large mass load; Chih-Shun Lu and Owen Lewis; J. Appl. Phys., vol. 43, No. 11; Nov. 1972; pp. 4385-4390.

\* cited by examiner

*Primary Examiner* — J M Saint Surin
(74) *Attorney, Agent, or Firm* — Hiscock & Barclay, LLP

(57) ABSTRACT

A method for accurately calculating the thickness of deposited thin film layers onto a piezoelectric crystal blank in which dissimilar materials can be utilized, enabling determinations for various applications employing exotic materials. Additionally, the specific acoustic impedance (or equivalent z-ratio) of an unknown deposited material can be determined. The exact analytical solution nearly eliminates thickness errors when several layers of different materials are sequentially deposited on the same monitor quartz crystal.

17 Claims, 6 Drawing Sheets

METHOD OF DETERMINING MULTILAYER THIN FILM DEPOSITION ON A PIEZOELECTRIC CRYSTAL

TECHNICAL FIELD OF THE APPLICATION

This invention relates generally to the field of thin film deposition and more specifically to the use of a piezoelectric crystal for measuring the mass of at least one deposited thin film layer. The herein described method enables the thickness of multiple layers of deposited materials, including dissimilar materials, to be determined and is applicable to quartz crystals as well as other suitable piezoids, including but not limited to, langasite, berlinite and gallium orthophosphate.

BACKGROUND OF THE APPLICATION

Thin Film Deposition Controllers which are based on Quartz Crystal Microbalance (QCM) have been in use for a very long time in the thin film coating industry such as described, for example, in U.S. Pat. No. 5,112,642 to Wajid and U.S. Pat. No. 5,869,763 to Vig et al., among others. In a typical arrangement, a monitor quartz crystal is placed in proximity to a substrate in a thin film deposition apparatus wherein the crystal and substrate are each coated at the same time. The material that is deposited on the crystal is usually proportional to the material which is deposited on the substrate. As a result of material deposition on the quartz crystal, its resonance frequency shifts downwards in a monotonic manner. Therefore, the knowledge of the frequency shift of the crystal along with the density of the material allows an estimation of the thickness of material that is deposited on the crystal and the substrate.

Previously, the subject matter of mass determination by a piezoelectric quartz crystal microbalance has been handled, for example by Lu and Czanderna in their treatise, *Applications of Piezoelectric Quartz Crystal Microbalances*. Earliest QCM instruments utilized the Sauerbrey relation in order to calculate deposited film's thickness from the resonant frequency shift of the quartz crystal. Sauerbrey's formula was accurate, however, only for a very limited frequency shift. In the 1970s, Lu and Lewis published an analysis that accounted for the elastic properties of the deposited film. The Lu-Lewis equation, trademarked as Zmatch® vastly improved the accuracy of QCM instruments and extended their useful range. As a result, nearly all QCM instruments intended for thin film deposition process control currently use the Zmatch equation for converting the frequency shift of a quartz crystal into the thickness of the deposited film.

However, the Zmatch equation is strictly valid with regard to the deposition of only one material on a quartz crystal. Deposition of two or more dissimilar materials in succession, compromises the accuracy of this relation. The extent of error depends on the extent of mismatch of the acoustic properties of deposited materials and the thickness of the layers that are deposited. Therefore and if a process requires different materials to be deposited on a substrate, a dedicated quartz crystal must be used exclusively for each material; particularly, if accuracy is paramount.

Over the years, the market for QCM-based thin film controllers have evolved. In recent times, its predominant use is found in the optical coating industry. An optical coating is usually a stack of many thin layers of dielectric materials, mostly oxides and fluorides. These materials are dissimilar in terms of their optical as well as their acoustic properties. Circumstances rarely permit users to dedicate one quartz crystal for each deposited material. However, compromising the accuracy of thickness/measurement is something that can not be afforded. As a result, optical coating houses use QCM for the deposition rate control and determine deposition process using an optical end-point detector, such as a reflectometer or ellipsometer.

In the early 1990s, the inventors of the present application created a process referred to as "Auto-Z", which partly overcame the above-noted limitation. However, Auto-Z is only an approximation that is based upon simultaneous evolution of two resonant frequencies of a quartz crystal. To that end, Auto-Z is useful in the deposition of multiple layers of materials with known acoustic properties, or materials of unknown acoustic properties or alloys of varying stoichiometry. However, Auto-Z is only an incremental improvement over the Zmatch equation and is not a substitute for an exact solution of the problem of multi-layer thin film deposition.

To the best of our knowledge, only thin film controllers such as those that are commercially sold by ULVAC Corporation presently make claims of multi layer control. A review of the commercially available ULVAC Model CRTM-9000 Controller indicates use of a linear extrapolation scheme. When a layer of different material is deposited, the slope of extrapolation is recalculated. All these calculations are done prior to actual deposition of the current layer. As described in the User's Manual for this controller, it may take up to tens of seconds to finish these background calculations. During deposition, the last calculated slope is multiplied by the frequency shift in order to estimate the thickness of the current layer. Thus, it is safe to conclude that these controllers do not use an analytically correct solution for multi-layer deposition.

There is also an ancillary problem associated with the deposition of thin film on a quartz crystal. The above-noted Zmatch equation requires precise knowledge regarding the specific acoustic impedance or its inverse ratio to that of AT-cut quartz (z-ratio) of the material to be deposited. The accuracy of the estimation of thickness/rate therefore directly depends on the accuracy of this physical property. The extent of error depends on the extent of mismatch of acoustic properties of deposited materials and the total thickness of the layers.

Another significant and growing use of QCM is in the emerging organic light emitting diode (OLED) manufacturing industry. OLED processes usually require use of fairly exotic organic materials. Some of these materials in fact are so new that their physical properties, such as, elastic modulus, shear wave velocity, specific acoustic impedance or even density are not definitively known.

A conventional Zmatch technique can be used to back calculate z-ratio or specific acoustic impedance of an unknown material, provided a thick layer (i.e., one micron or more) is deposited on the quartz crystal. This is necessary to minimize the impact of acoustic impedance mismatch at the electrode-film boundary. OLED materials, on the other hand, are light weight and highly damping. Thus, the deposited layers are often thin and the associated mass load is less than that of the electrode itself. Thus, conventional methods will be highly error prone in this case.

SUMMARY OF THE APPLICATION

One aspect described herein is the provision of a comprehensive analytically exact solution to the problem of multiple layer deposition on a quartz or other piezoelectric crystal.

According to this solution, the thickness of the layer currently being deposited is determined based upon the knowledge of acoustic phase lag through all the layers that have been previously deposited.

According to one version, a method for determining the thickness of a material layer onto a piezoelectric blank is provided, the method including the steps of:

provide a piezoelectric crystal blank;

determining the fundamental resonance frequency of said crystal blank;

applying an electrode to the crystal blank and determining the resonance frequency of the crystal blank and applied electrode;

applying a first deposited thin film layer onto said crystal blank;

determining the resonance frequency of the composite resonator comprising said blank, said electrode and said deposited layer;

determining acoustic phase lag across the crystal blank, the electrode and the deposited layer as computed at said resonance frequency, and computing the layer's thickness from the phase lag information computed in the previous step and density of the material.

Preferably, the tangent functions of the phase lags across the crystal blank, electrode and deposited layer are computed and combined algebraically. Arctangent functions of the prior step yields equivalent phase lags through the layer currently being deposited.

The intrinsic resonance frequency of the deposited layer can subsequently be determined from the thickness computation.

Any number of subsequent layers can be deposited in which the thickness of each layer can be determined in a similar manner.

The deposition of any particular thin film layer can also be determined such that the rate of deposition can be determined at any time $\Delta t$ during the deposition process from at least two successive thickness measurements wherein computed values of thickness can algebraically be combined over $\Delta t$.

According to another aspect of the herein described invention, a method for determining the specific acoustic impedance of an unknown material by thin film deposition on a piezoelectric crystal blank is provided, the method comprising the steps of:

providing a piezoelectric crystal blank having a specific acoustic impedance;

measuring the fundamental resonance frequency of said piezoelectric crystal blank;

applying an electrode having a specific acoustic impedance and density to said crystal blank;

measuring the fundamental resonance frequency of said crystal blank and applied electrode;

computing acoustic phase lag information across said crystal blank and said applied electrode at said resonance frequency;

determining the thickness of said electrode based on said computed acoustic phase lag information and the density of said electrode;

determining the mass of said crystal blank and said applied electrode;

depositing a layer of material having unknown acoustic impedance and unknown density onto said previously applied electrode and crystal blank;

measuring the fundamental resonant frequency of said composite resonator comprising said crystal blank, said electrode and said deposited layer;

weighing said crystal blank, said applied electrode and said deposited layer;

determining the mass of said deposited layer based on said weight measurements;

determining the area of the deposited layer on said crystal blank;

estimating the thickness of said deposited layer based on the determined mass and area measurements;

computing acoustic phase lag information across the crystal blank, said electrode and said deposited layer at said measured resonant frequency; and determining the specific acoustic impedance of said deposited film layer based upon said phase lag information and said thickness measurement.

According to one version, a nonlinear equation is constructed following the computation of the acoustic phase lag through each of the various layers in which the specific acoustic impedance can be determined, using an iterative root solving method.

One advantageous benefit realized by the herein described method is unprecedented accuracy in the deposition of multiple layers on a single quartz or other piezoelectric crystal.

Yet another advantage is that improved accuracy is realized even for a very thin single material layer, as appropriate acoustic property is assigned to the underlying electrodes.

The herein described solution can be determined in real time using existing equipment already used in making thin film thickness determinations.

Moreover, the herein described technique permits accurate determination of an unknown material's acoustic impedance, enabling use of the technique in OLED and other processes.

According to the method elucidated herein, the impact of applied electrodes is naturally accounted for. Moreover, the herein described method can accurately back calculate the specific acoustic impedance of an unknown material, even when the deposited film is thin.

These and other features and advantages will be readily apparent from the following Detailed Description, which should be read in conjunction with the accompanying drawings.

DETAILED DESCRIPTION

The following relates to a preferred method for determining the thickness of various materials, including dissimilar materials, which are applied to a substrate as well as a related method for determining the z-ratio of an unknown material deposited on a substrate. Several terms are used throughout the course of the description in order to provide a suitable frame of reference in regard to the accompanying drawings. It is not intended that these terms should be overlimiting in terms of their scope or effect, except where so specifically indicated.

Figure 1:
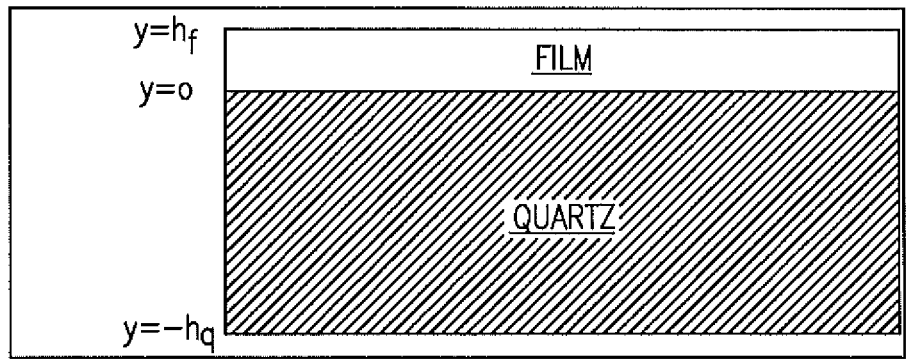
FIG. 1 depicts an exemplary piezoelectric (quartz) crystal having thickness $h_q$ and a deposited layer of thickness shown as $h_f$.
Figure 2:
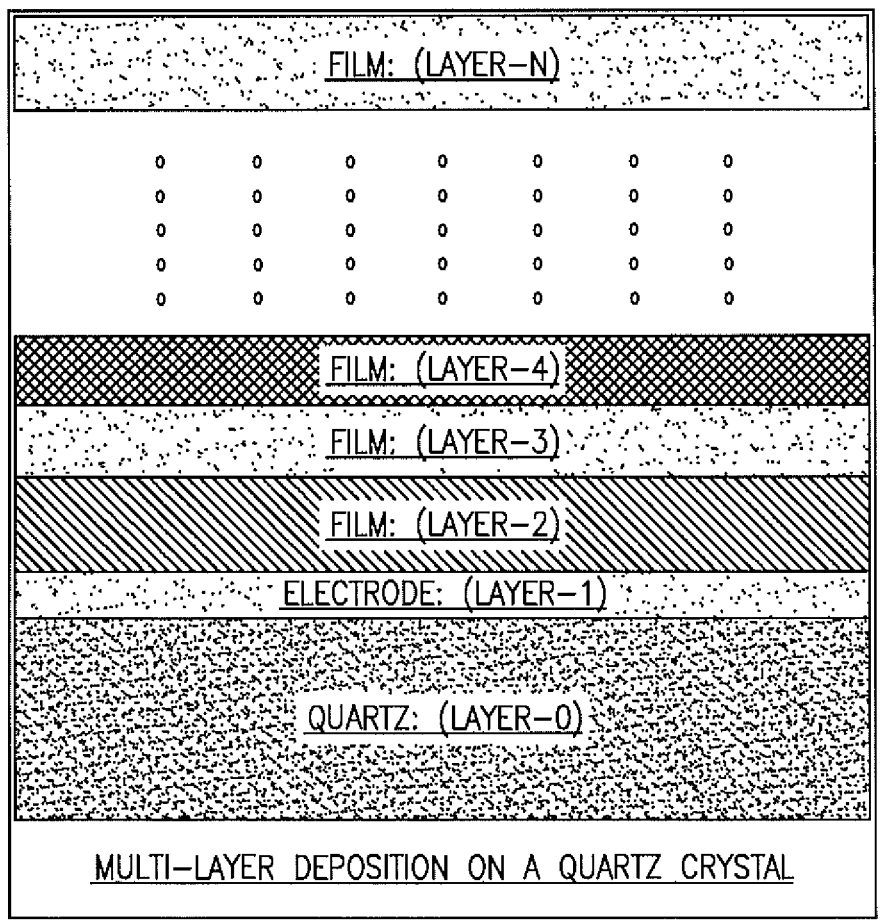
FIG. 2 schematically depicts multiple layers of film as typically deposited on a quartz crystal blank and electrode.
Figure 3:
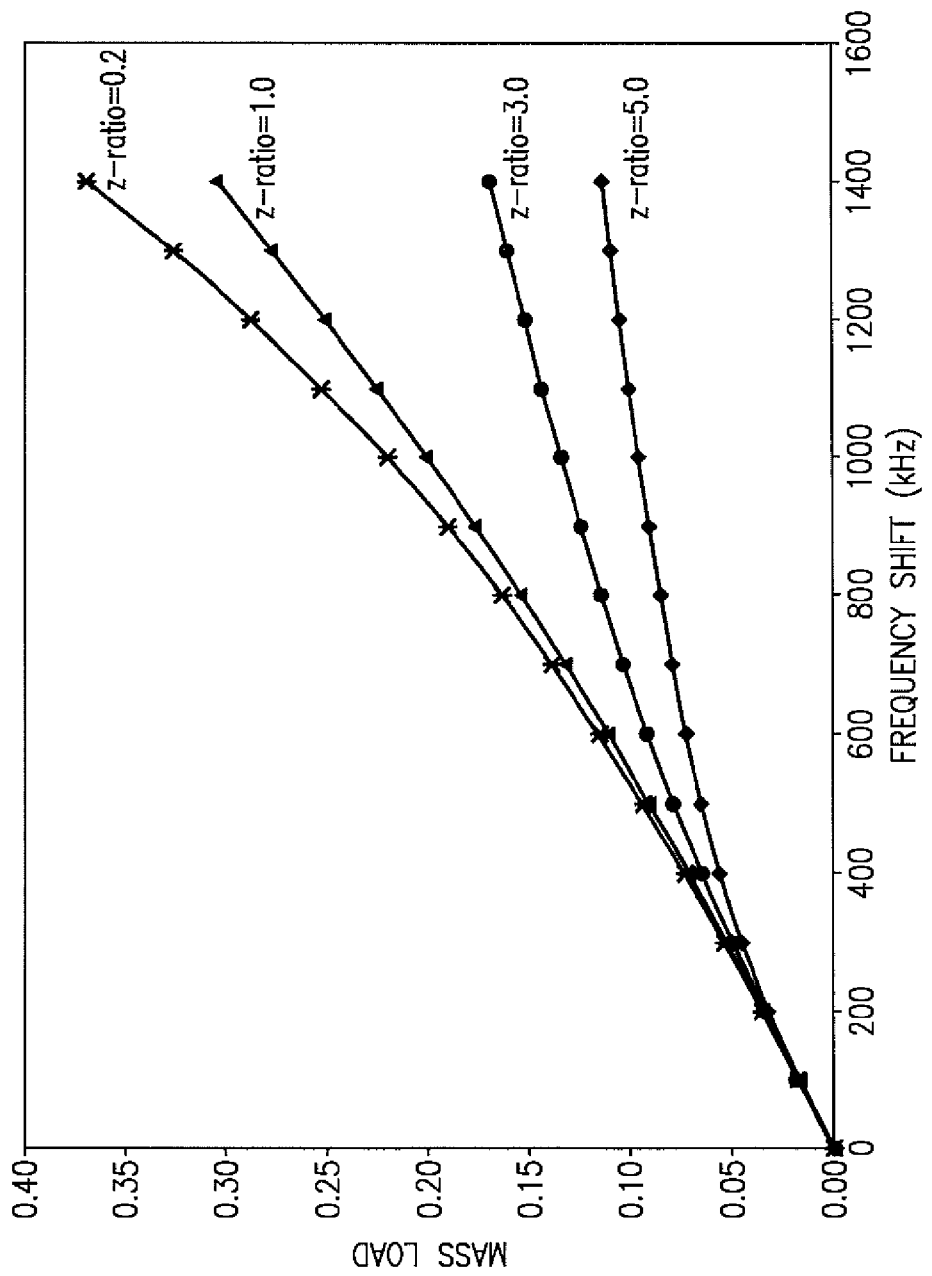
FIG. 3 graphically illustrates mass load (proportional to the product of film thickness and its density) vs. frequency shift on a piezoelectric crystal due to material deposition for various values of z-ratio.

In a preferred embodiment described herein, a AT-cut quartz crystal blank is utilized, which is a de-facto industry standard. However, it should be noted that this standard represents merely an exemplary version and therefore the teachings discussed herein are also equally applicable to other crystal cuts, such as but not limited to, SC-, IT-, FC-, RT- and other crystal cuts for any suitable piezoelectric material (including but not limited to langasite, berlinite, and gallium orthophosphate), such as used for mass sensing purposes. As described in greater detail herein the exemplary quartz crystal blank, applied electrode(s) and the deposited layers of thin film, such as shown in FIG. 2, combine to form a compound resonator.

An apparatus utilizing an active oscillator and a frequency counter or a phase-locked loop apparatus such as manufactured by Inficon, Inc., among others, are required in order to determine the resonance frequency of this compound or composite resonator. Measurements made by the apparatus can be done in real time; typically, on the order of about 10 measurements per second. However, the measurement frequency can be varied sufficiently, depending upon the application and the processing power of the instrument/apparatus which is utilized.

Mathematical Details:
Zmatch Equation:

For background purposes and completeness, the prior developed Zmatch equation is briefly summarized. As previously noted, Lu and Czanderna have thoroughly dealt with the subject matter of mass determination by a piezoelectric quartz crystal microbalance in their treatise, *Applications of Quartz Crystal Microbalances*. They have given a general derivation of the so called Lu-Lewis equation. This Zmatch equation can be written in the following form and forms the basis of many commercial thin film controllers that are presently available:

$$h_f = -\frac{Z_f}{2\pi f \rho_f} \arctan\left(\frac{Z_q}{Z_f} \tan\left(\frac{\pi f}{f_q}\right)\right) \quad (1.1)$$

In the preceding relation, $h_f$, $\rho_f$ and $Z_f$ represent the thickness, density and specific acoustic impedance of the deposited film respectively, and f, $Z_q$ and $f_q$ represent current measurement frequency, the specific acoustic impedance of quartz and the resonance frequency of the quartz blank alone, respectively. Due to its superior thermal properties and simplicity of manufacturing, the AT-cut quartz crystal has long established itself as the industry standard and is used for purposes of this background discussion. The specific acoustic impedance $Z_q$ of AT-cut quartz is 8,765,000 kg/m²/s. It is customary to express the specific acoustic impedance of other thin film materials as the inverse ratio of that of AT-cut quartz. This inverse ratio is also commonly referred to as the acoustic impedance ratio or z-ratio (z). Equation (1.1) can then be rewritten in terms of the z-ratio as:

$$h_f = -\frac{Z_q}{2\pi z f \rho_f} \arctan\left(z \tan\left(\frac{\pi f}{f_q}\right)\right) \quad (1.2)$$

Acoustic Transfer Matrix

It will be shown that the same result (equation (1.1)) can be derived by the use of an acoustic transfer matrix. In this formalism, the quartz crystal and subsequent films may be considered as waveguides having equal cross-sectional area. The object of the acoustic transfer matrix is to relate a state vector comprising of a set of dynamic variables at the entry port of the waveguide with that at the exit port of the waveguide. If force (F) and displacement velocity (u̇) are chosen as pertinent variables, then the following relationship holds:

$$\begin{bmatrix} F_1 \\ \dot{u}_1 \end{bmatrix} = \begin{bmatrix} \cos(\theta) & jZ\sin(\theta) \\ j\sin(\theta)/Z & \cos(\theta) \end{bmatrix} \begin{bmatrix} F_2 \\ \dot{u}_2 \end{bmatrix} \quad (2.1)$$

In the preceding, Z refers to the specific acoustic impedance while $\theta = kh = \omega t$ represents the acoustic phase lag through the width of the waveguide. Resonance frequency is found by setting the force at the free surfaces to be zero; that is, $F_1=0$ and $F_2=0$. When two such waveguides or resonators are stacked upon each other, continuity of force and displacement velocity is automatically enforced. For example, if the quartz is assumed to be the waveguide-0 and the thin film is assumed to be the waveguide-1, then $$\begin{bmatrix} F_0 \\ \dot{u}_0 \end{bmatrix} = \begin{bmatrix} \cos(\theta_0) & jZ_0\sin(\theta_0) \\ j\sin(\theta_0)/Z_0 & \cos(\theta_0) \end{bmatrix} \begin{bmatrix} F_1 \\ \dot{u}_1 \end{bmatrix} \quad (2.2)$$

$$\begin{bmatrix} F_1 \\ \dot{u}_1 \end{bmatrix} = \begin{bmatrix} \cos(\theta_1) & jZ_1\sin(\theta_1) \\ j\sin(\theta_1)/Z_1 & \cos(\theta_1) \end{bmatrix} \begin{bmatrix} F_2 \\ \dot{u}_2 \end{bmatrix}$$

Then we have $$\begin{bmatrix} F_0 \\ \dot{u}_0 \end{bmatrix} = \begin{bmatrix} \cos(\theta_0) & jZ_0\sin(\theta_0) \\ j\sin(\theta_0)/Z_0 & \cos(\theta_0) \end{bmatrix} \begin{bmatrix} \cos(\theta_1) & jZ_1\sin(\theta_1) \\ j\sin(\theta_1)/Z_1 & \cos(\theta_1) \end{bmatrix} \quad (2.3)$$

$$\begin{bmatrix} F_2 \\ \dot{u}_2 \end{bmatrix} = \begin{bmatrix} \cos(\theta_0)\cos(\theta_1) - \frac{Z_0}{Z_1}\sin(\theta_0)\sin(\theta_1) & j\{Z_0\sin(\theta_0)\cos(\theta_1) + Z_1\sin(\theta_1)\cos(\theta_0)\} \\ j\{\sin(\theta_0)\cos(\theta_1)/Z_0 + \sin(\theta_1)\cos(\theta_0)/Z_1\} & \cos(\theta_0)\cos(\theta_1) - \frac{Z_1}{Z_0}\sin(\theta_0)\sin(\theta_1) \end{bmatrix} \begin{bmatrix} F_2 \\ \dot{u}_2 \end{bmatrix}$$

By setting $F_0 = F_2 = 0$, $Z_0 \sin(\theta_0)\cos(\theta_1) + Z_1 \sin(\theta_1)\cos(\theta_0) = 0$, or $Z_0 \tan(\theta_0) + Z_1 \tan(\theta_1) = 0$, or $Z_1 \tan(\theta_1) = -Z_0 \tan(\theta_0)$ \quad (2.4)

The phase lag terms can be further expanded ($C_q$ and $C_f$ being the shear wave speed in quartz and the film, respectively), as follows:

$$\theta_0 = \omega t = \frac{\omega h_q}{C_q} = \frac{\pi f}{f_q} \quad (2.5)$$

$$\theta_1 = \frac{\omega h_f}{C_f} = \frac{2\pi f \rho_f h_f}{Z_f}$$

Then, combining equations (2.4) and (2.5) will lead to an identical expression as in (1.1). There is a considerable space saving if we adopt the following abbreviated notations:

$$C_i = \cos(\theta_i), S_i = \sin(\theta_i), T_i = \tan(\theta_i) \quad (2.6)$$

Equation (2.3) can be written in this notation as $$\begin{bmatrix} F_0 \\ \dot{u}_0 \end{bmatrix} = \begin{bmatrix} C_0 C_1 - \frac{Z_0}{Z_1} S_0 S_1 & j\{Z_0 S_0 C_1 + Z_1 S_1 C_0\} \\ j\{S_0 C_1/Z_0 + S_1 C_0/Z_1\} & C_0 C_1 - \frac{Z_1}{Z_0} S_0 S_1 \end{bmatrix} \begin{bmatrix} F_2 \\ \dot{u}_2 \end{bmatrix} \quad (2.7)$$

The requirement of traction free end surfaces will render the upper right-hand element in the resultant matrix to be zero, yielding (as in equation (2.4))

$$Z_0 S_0 C_1 + Z_1 S_1 C_0 = 0, \text{ or} \quad (2.8)$$

$$-Z_1 T_1 = Z_0 T_0 \quad (2.8a)$$

Application of subsequent layers means that the transfer matrix in equation (2.7) will have to be post-multiplied by another transfer matrix like in (2.1) pertinent to the newly deposited layer and the upper right-hand element in the resultant matrix will have to be set to zero for resonance condition. Applying this scheme for a 3-layer system, the following transfer matrix is obtained:

$$\begin{bmatrix} C_0 C_1 - \frac{Z_0}{Z_1} S_0 S_1 & j\{Z_0 S_0 C_1 + Z_1 S_1 C_0\} \\ j\{S_0 C_1/Z_0 + S_1 C_0/Z_1\} & C_0 C_1 - \frac{Z_1}{Z_0} S_0 S_1 \end{bmatrix} \begin{bmatrix} C_2 & jZ_2 S_2 \\ jS_2/Z_2 & C_2 \end{bmatrix} = \quad (2.9)$$

$$\begin{bmatrix} \left(C_0 C_1 - \frac{Z_0}{Z_1} S_0 S_1\right)C_2 - (Z_0 S_0 C_1 + Z_1 S_1 C_0)S_2/Z_2 & j\left\{\left(C_0 C_1 - \frac{Z_0}{Z_1} S_0 S_1\right)Z_2 S_2 + (Z_0 S_0 C_1 + Z_1 S_1 C_0)C_2\right\} \\ j\left\{\left(C_0 C_1 - \frac{Z_1}{Z_0} S_0 S_1\right)S_2/Z_2 + (S_0 C_1/Z_0 + S_1 C_0/Z_1)C_2\right\} & \left(C_0 C_1 - \frac{Z_1}{Z_0} S_0 S_1\right)C_2 - (S_0 C_1/Z_0 + S_1 C_0/Z_1)Z_2 S_2 \end{bmatrix}$$

Therefore, the resonance condition requires that $$\left(C_0 C_1 - \frac{Z_0}{Z_1} S_0 S_1\right)Z_2 S_2 + (Z_0 S_0 C_1 + Z_1 S_1 C_0)C_2 = 0 \quad (2.10)$$

Leading to $$-Z_2 T_2 = \frac{Z_0 T_0 + Z_1 T_1}{1 - \frac{Z_0}{Z_1} T_0 T_1} \quad (2.10a)$$

Continuing in this manner, we get for subsequent layers, $$-Z_3 T_3 = \frac{(Z_0 T_0 + Z_1 T_1 + Z_2 T_2) - \frac{Z_0 Z_2}{Z_1} T_0 T_1 T_2}{1 - \left(\frac{Z_0}{Z_1} T_0 T_1 + \frac{Z_0}{Z_2} T_0 T_2 + \frac{Z_1}{Z_2} T_1 T_2\right)} \quad (2.11)$$

$$-Z_4 T_4 = \frac{(Z_0 T_0 + Z_1 T_1 + Z_2 T_2 + Z_3 T_3) - \left(\frac{Z_0 Z_2}{Z_1} T_0 T_1 T_2 + \frac{Z_0 Z_3}{Z_1} T_0 T_1 T_3 + \frac{Z_0 Z_3}{Z_2} T_0 T_2 T_3 + \frac{Z_1 Z_3}{Z_2} T_1 T_2 T_3\right)}{1 - \left(\frac{Z_0}{Z_1} T_0 T_1 + \frac{Z_0}{Z_2} T_0 T_2 + \frac{Z_0}{Z_3} T_0 T_3 + \frac{Z_1}{Z_2} T_1 T_2 + \frac{Z_1}{Z_3} T_1 T_3 + \frac{Z_2}{Z_3} T_2 T_3\right) + \frac{Z_0 Z_2}{Z_1 Z_3} T_0 T_1 T_2 T_3} \quad (2.12)$$

$$-Z_5T_5 = \frac{(Z_0T_0 + Z_1T_1 + Z_2T_2 + Z_3T_3 + Z_4T_4) - \left(\frac{Z_0Z_2}{Z_1}T_0T_1T_2 + \frac{Z_0Z_3}{Z_1}T_0T_1T_3 + \frac{Z_0Z_4}{Z_1}T_0T_1T_4 + \frac{Z_0Z_3}{Z_2}T_0T_2T_3 + \frac{Z_0Z_4}{Z_2}T_0T_2T_4 + \frac{Z_0Z_4}{Z_3}T_0T_3T_4 + \frac{Z_1Z_3}{Z_2}T_1T_2T_3 + \frac{Z_1Z_4}{Z_2}T_1T_2T_4 + \frac{Z_2Z_4}{Z_3}T_2T_3T_4\right)}{1 - \left(\frac{Z_0}{Z_1}T_0T_1 + \frac{Z_0}{Z_2}T_0T_2 + \frac{Z_0}{Z_3}T_0T_3 + \frac{Z_0}{Z_4}T_0T_4 + \frac{Z_1}{Z_2}T_1T_2 + \frac{Z_1}{Z_3}T_1T_3 + \frac{Z_1}{Z_4}T_1T_4 + \frac{Z_2}{Z_3}T_2T_3 + \frac{Z_2}{Z_4}T_2T_4 + \frac{Z_3}{Z_4}T_3T_4\right) + \left(\frac{Z_0Z_2}{Z_1Z_3}T_0T_1T_2T_3 + \frac{Z_0Z_2}{Z_1Z_4}T_0T_1T_2T_4 + \frac{Z_0Z_3}{Z_1Z_4}T_0T_1T_3T_4 + \frac{Z_0Z_3}{Z_2Z_4}T_0T_2T_3T_4 + \frac{Z_1Z_3}{Z_2Z_4}T_1T_2T_3T_4\right)}$$

(2.13)

Equations for subsequent layers will be enormously long, as is apparent from the foregoing. However, a general recursive relation for any arbitrary layer can be written in the following manner:

$$-Z_N T_N = \frac{\sum_{i=0}^{N-1} Z_i T_i - \sum_{i=0}^{N-1}\sum_{j>i}^{N-1}\sum_{k>j}^{N-1} \frac{Z_i Z_k}{Z_j} T_i T_j T_k + \sum_{i=0}^{N-1}\sum_{j>i}^{N-1}\sum_{k>j}^{N-1}\sum_{l>k}^{N-1}\sum_{m>l}^{N-1} \frac{Z_i Z_k Z_m}{Z_j Z_l} T_i T_j T_k T_l T_m - \ldots}{1 - \sum_{i=0}^{N-1}\sum_{j>i}^{N-1} \frac{Z_i}{Z_j} T_i T_j + \sum_{i=0}^{N-1}\sum_{j>i}^{N-1}\sum_{k>j}^{N-1}\sum_{l>k}^{N-1} \frac{Z_i Z_k}{Z_j Z_l} T_i T_j T_k T_l - \ldots} = K$$

(2.14)

In the foregoing relation, N refers to the index of the layer currently being deposited and i, j, k, l, m are "dummy" indices indicating previously deposited layers. The composite parameter K signifies the totality of phase lag through all previously deposited layers.

On the right hand side of the equation, odd order terms appear in the numerator with alternating signs and even order terms are in the denominator with alternating signs. Z combinations follow the order of the layers from the lowest to the highest.

To summarize the above-noted procedure, equation (2.14) will yield a phase lag $\theta_N$ for the Nth layer in terms of phase lags in all previous layers, including the electrode and the quartz blank.

Then, from the definition of phase lag, the thickness of the Nth layer can be deduced, as follows:

$$h_N = \frac{Z_N \theta_N}{2\pi f \rho_N} = -\frac{Z_N}{2\pi f \rho_N} \arctan(K/Z_N)$$

(2.17)

For those layers which are already deposited, the thickness is already known and the phase lag would then depend on the driving frequency alone. It can be conveniently written if an intrinsic resonant frequency of each deposited layer is defined such that:

$$fr_i = \frac{Z_i}{2h_i \rho_i}$$

(2.18)

and $$\theta_i = \frac{\pi f}{fr_i}$$

To illustrate the dramatic difference in the calculated thickness by the method above in comparison to traditional Zmatch method, the following Table I depicts differences based on upon simulated deposition of multiple layers of different materials on a quartz crystal with gold electrodes between a Zmatch analysis and the present technique (referred to as "MultiZ" in Table I), as described above in a copper-calcium-tungsten-aluminum layered system. Clearly, the discrepancy (i.e., difference) between each layer thickness result as listed in the right most column of Table I is very substantial.

TABLE I

| | Density (g/cc) | z-ratio | Frequency (kHz) | Layer thickness Zmatch (kA) | Layer thickness MultiZ (kA) | Discrepancy |
|---|---|---|---|---|---|---|
| Quartz blank | | 1.00 | 6045 | | | |
| Gold electrode | 19.3 | 0.381 | 5985 | 3.77 | 3.77 | |
| Copper layer | 8.93 | 0.437 | 5750 | 33.78 | 33.78 | 0.0% |
| Calcium layer | 1.55 | 2.62 | 5500 | 177.09 | 222.71 | −20.5% |
| Tungsten layer | 19.3 | 0.163 | 5250 | 22.03 | 17.18 | 28.2% |
| Aluminum layer | 2.7 | 1.08 | 5050 | 118.85 | 97.26 | 22.2% |

Figure 4:
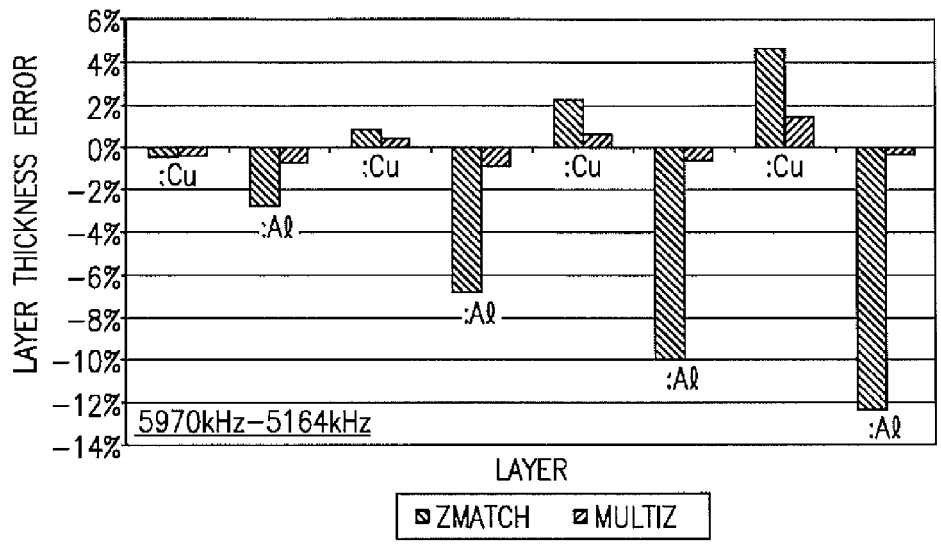
FIGS. 4-7 depicts the comparison of layer thickness error of traditional Zmatch technique and the herein described method. Each figure represents results of one experiment of alternating deposition of dissimilar materials, in which the error is computed with respect to gravimetric measurements.
Figure 5:
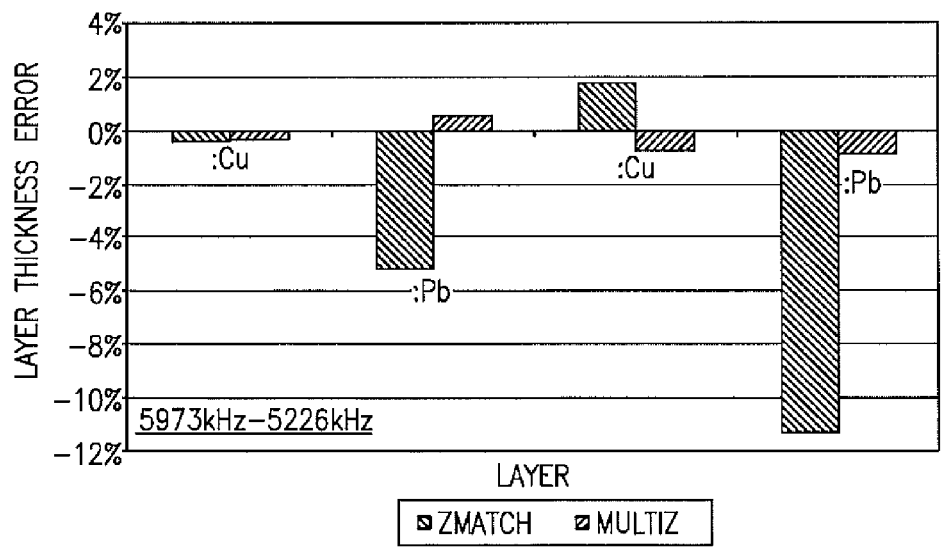
Figure 6:
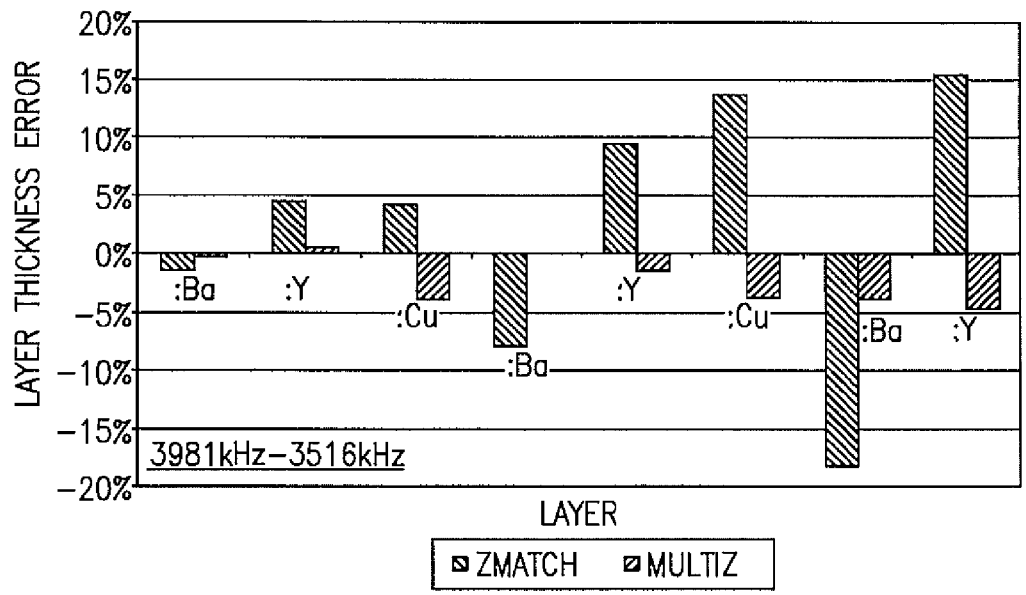
Figure 7:
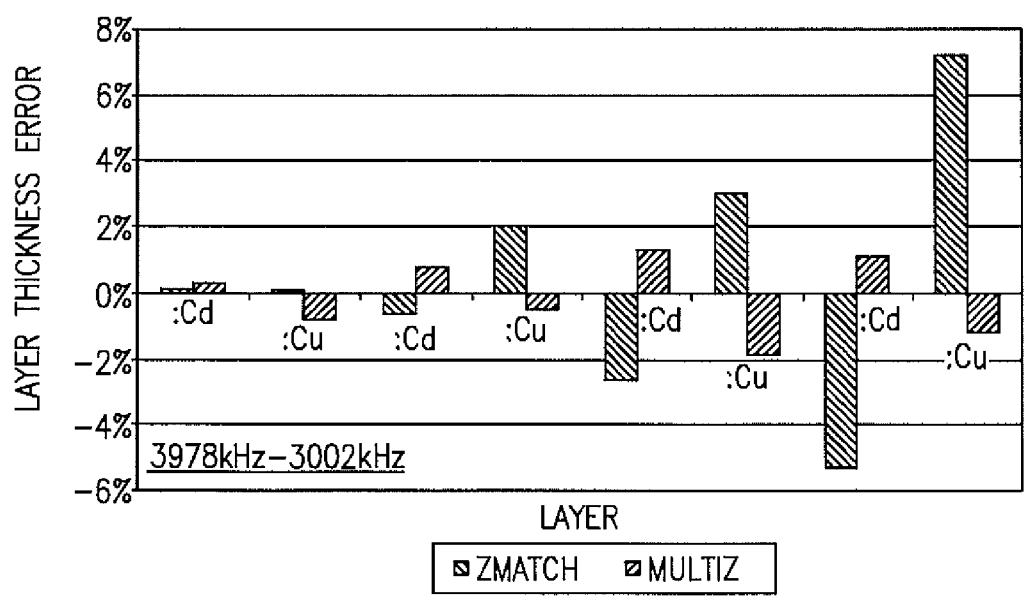

Comparison of the determined thickness as computed by these two techniques with gravimetric measurements is graphically presented in FIGS. 4-7, which clearly shows the superiority of the method presented herein. FIG. 4 represents a simulated comparison of thickness error in a copper-aluminum alternating layered system showing the application of each layer as viewed from left to right. FIG. 5 represents a similar simulated comparison for a copper-lead alternating layered system, while FIG. 6 represents a similar simulated comparison for a barium-yttrium-copper alternating layered system and FIG. 7 represents another simulated comparison for a cadmium-copper alternating layered system.

Figure 8:
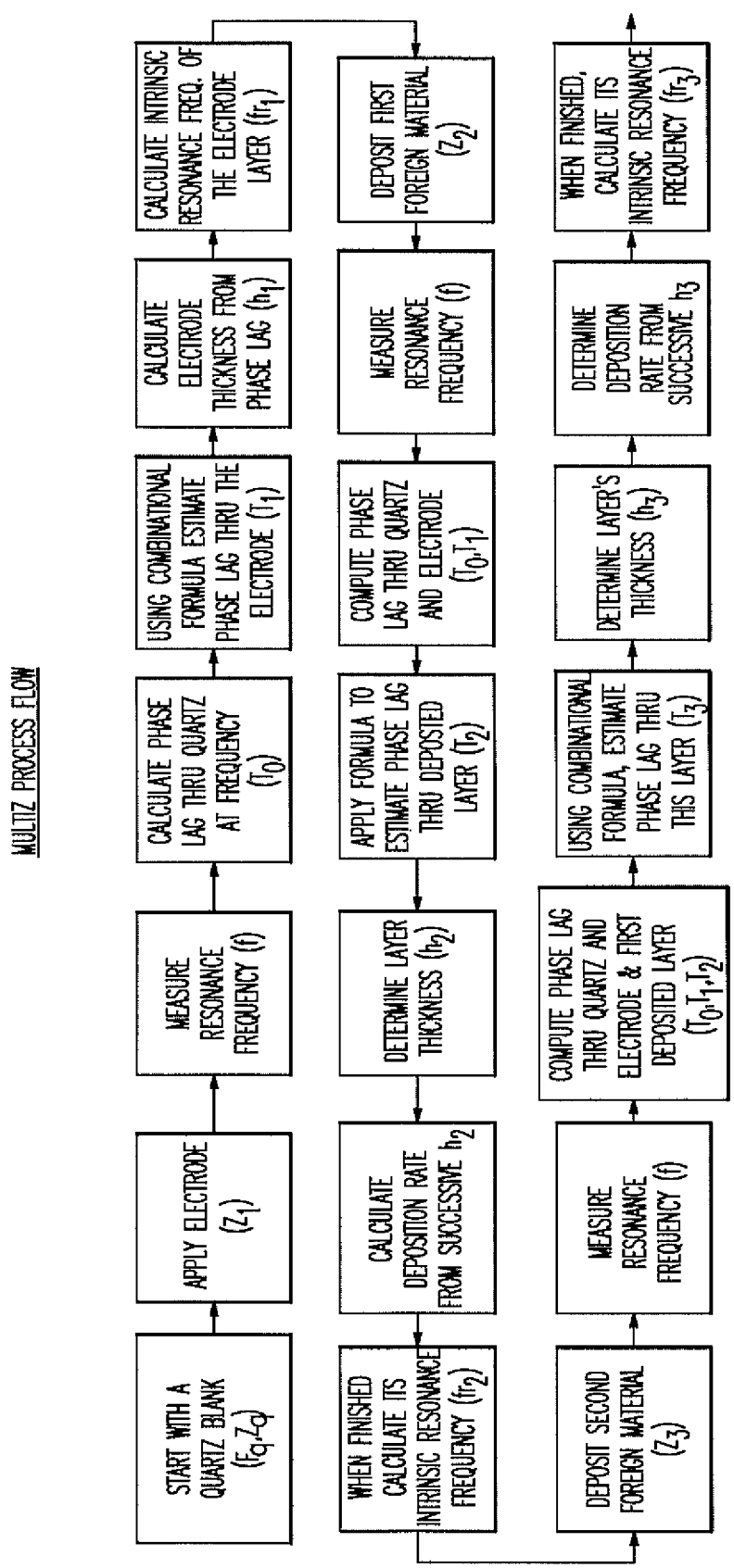
FIG. 8 is a flow chart depicting steps for determining the thickness of various layers of material, including dissimilar materials, on a piezoelectric crystal blank in accordance with the invention.

Referring to the flow chart presented in FIG. 8, the method for determining thickness for a multi layered crystal, such as those depicted according to each of the preceding examples is as follows: First, a quartz blank, such as an AT-cut crystal blank is provided, the blank being defined as layer-0 according to FIG. 2, which is characterized by its blank resonance frequency $F_q$ and specific acoustic impedance which is $Z_0=Z_q$.

The fundamental resonance frequency of this blank is then measured, such as in an air-gap fixture (not shown). Alternatively and in lieu of making this measurement, the blank can be designed to have a specific fundamental frequency within a very narrow range. An electrode layer (shown as layer-1 in FIG. 2) is then applied by conventional means onto the quartz blank wherein the electrode layer material is defined by a specific acoustic impedance, $Z_1$ and a density $\rho_1$. The resonance frequency of the quartz blank and electrode is then measured in the air gap or other suitable fixture, this frequency being designated herein as f.

The tangent of phase lag through the quartz blank (layer-0) at the measured frequency f is then determined using the relation $$T_0 = \tan\left(\frac{\pi f}{f_q}\right).$$

Applying equation (2.8a), in which $-Z_1T_1=Z_0T_0=K_0$ provides a determination of acoustic phase lag through the applied electrode layer wherein the electrode thickness can be determined using the relation $$h_1 = -\frac{Z_1}{2\pi f \rho_1}\arctan\left(\frac{K_0}{Z_1}\right)$$

The intrinsic resonance frequency of the electrode can then be estimated based on the relation $$fr_1 = \frac{Z_1}{2h_1\rho_1}$$

A first foreign material, shown as layer-2 pictorially according to FIG. 2, can then be deposited onto the electrode and crystal blank, this material being characterized by a specific acoustic resonance $Z_2$ and density $\rho_2$. The resonance frequency f of this composite resonator can be determined again using an air gap or other suitable fixture. Following this determination, acoustic phase lag information is computed through each of the previous layers according to the relations:

$$T_0 = \tan\left(\frac{\pi f}{f_q}\right)$$

and $$T_1 = \tan\left(\frac{\pi f}{fr_1}\right),$$

for each of the blank and electrode layer, respectively.

From the preceding, the combinational formula $$-Z_2T_2 = \frac{Z_0T_0 + Z_1T_1}{1 - \frac{Z_0}{Z_1}T_0T_1} = K_1$$

is used in order to determine the acoustic phase lag through the deposited layer.

The thickness of layer-2 can then be determined using equation $$h_2 = -\frac{Z_2}{2\pi f \rho_2}\arctan\left(\frac{K_1}{Z_2}\right)$$

In order to determine deposition rate of material, the following additional steps can be utilized. Following an interval $\Delta t$, the resonance frequency f' can be measured, again using the air gap or other suitable fixture and each of the prior steps are repeated wherein the acoustic phase lag information through the previous layers and the deposited layer can be computed at this measured frequency. The thickness of layer-2 can then be determined using the relation:

$$h_2' = -\frac{Z_2}{2\pi f' \rho_2}\arctan\left(\frac{K_1'}{Z_2}\right)$$

The deposition rate can then be determined as $(h_2'-h_2)/\Delta t$ wherein the above process are repeated at predetermined intervals until the end of the deposition of this layer.

Finally, the intrinsic resonance frequency of layer-2 can be determined using the relation:

$$fr_2 = \frac{Z_2}{2h_2\rho_2}$$

A second foreign material (layer-3 as shown in FIG. 2), characterized by $Z_3$ and $\rho_3$ is then subsequently deposited onto the crystal and onto layer-2 thereof. As in the preceding, the resonance frequency f of the composite resonator is first measured using the air gap or other suitable fixture. Acoustic phase lag information through each of the previous layers (layers 0, 1, 2), is then computed using the relations:

$$T_0 = \tan\left(\frac{\pi f}{f_q}\right),$$

$$T_1 = \tan\left(\frac{\pi f}{fr_1}\right),$$

$$T_2 = \tan\left(\frac{\pi f}{fr_2}\right),$$

respectively.

Following this computation, the combinational formula $$-Z_3T_3 = \frac{(Z_0T_0 + Z_1T_1 + Z_2T_2) - \frac{Z_0Z_2}{Z_1}T_0T_1T_2}{1 - \left(\frac{Z_0}{Z_1}T_0T_1 + \frac{Z_0}{Z_2}T_0T_2 + \frac{Z_1}{Z_2}T_1T_2\right)} = K_2$$

is applied in order to determine the phase lag of the newly deposited layer.

The layer's thickness can then be determined as:

$$h_3 = -\frac{Z_3}{2\pi f \rho_3} \arctan\left(\frac{K_2}{Z_3}\right)$$

As in the instance of the preceding layer-2, deposition rate of layer-3 can be calculated throughout by measuring the resonance frequency f' after a time interval Δt, recomputing the phase lag information through each of the previous layers at this measured frequency, applying the combination formula to determine phase lag through the deposited layer and determining the thickness of the layer as:

$$h_3' = -\frac{Z_3}{2\pi f' \rho_3} \arctan\left(\frac{K_2'}{Z_3}\right)$$

and then determining the deposition rate as $(h_3'-h_3)/\Delta t$.

Finally, the intrinsic resonance frequency of layer-3 is back calculated using the relation:

$$fr_3 = \frac{Z_3}{2h_3\rho_3}$$

It will be readily apparent that the thickness and deposition rate of any subsequent foreign material layer (layer 4, 5, 6, ... n) can be determined, as well as its intrinsic resonance frequency, according to similar applications of the prior steps, as described in the foregoing description.

Figure 9:
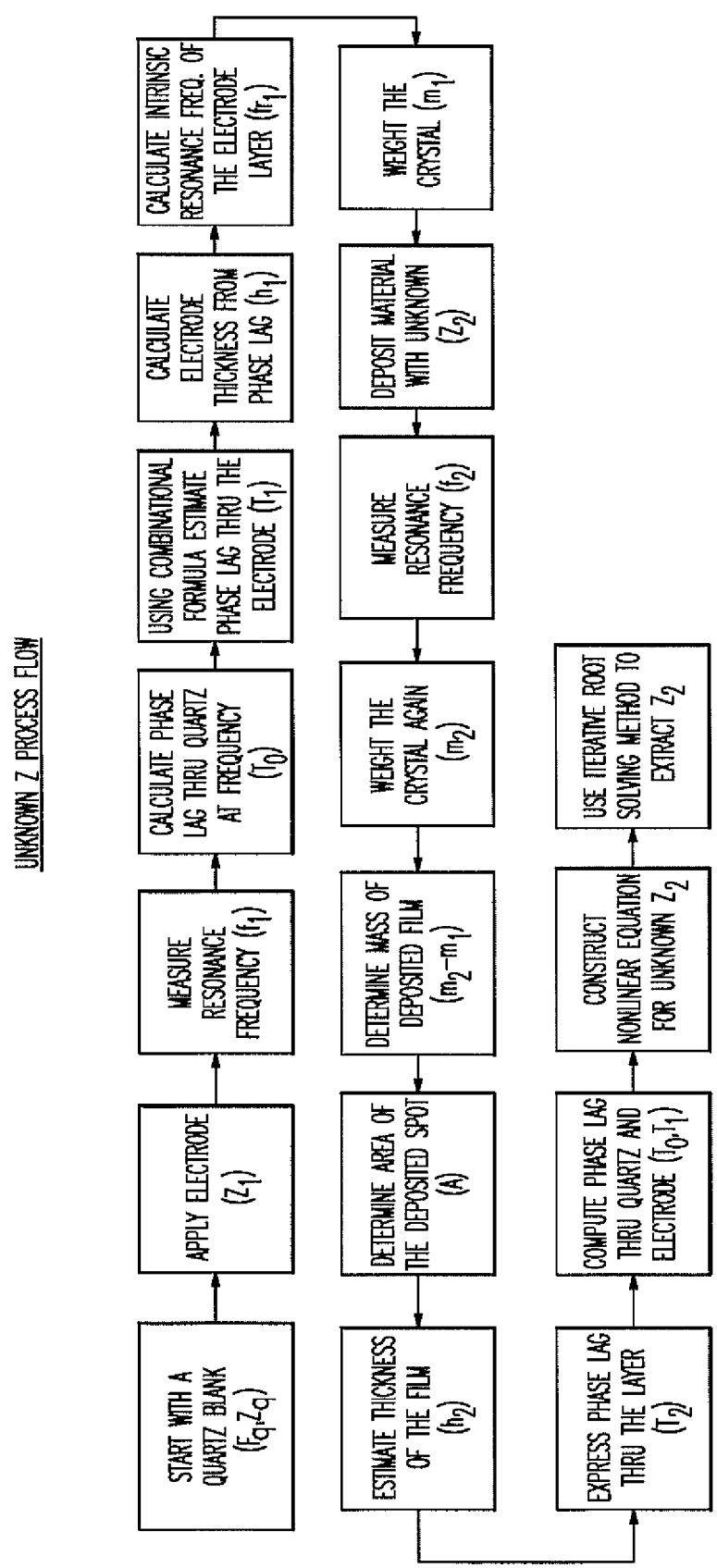
FIG. 9 is a flow chart depicting steps for determining the z-ratio of a deposited layer of an unknown material onto a crystal blank in accordance with the invention.

Referring to FIG. 9, the steps that are necessary to implement a solution for the ancillary problem of determining the specific acoustic impedance of an unknown material are as follows. As in the preceding, an apparatus utilizing an active oscillator and a frequency counter or a phase-locked loop apparatus is required in this instance in order to determine the resonance frequency of the composite resonator which is defined by the quartz (piezoelectric) blank, electrode(s) and each layer of deposited thin film(s).

First, the quartz blank is made available, such as an AT-cut quartz blank having a specific acoustic impedance $Z_q=Z_0$. The fundamental resonance frequency of the quartz blank is initially measured in an air-gap fixture ($f_q$). Alternatively, the blank can be designed to possess a specific fundamental frequency within a very narrow range in lieu of this measurement step. Following application of an electrode by known means wherein the electrode has a specific acoustic impedance of $Z_1$ and a density $\rho_1$, the resonance frequency ($f_1$) of the quartz blank and applied electrode is measured again. As in the preceding, acoustic phase lag information is computed through the quartz blank at the above measured frequency, using the relation $$T_0 = \tan\left(\frac{\pi f_1}{f_q}\right)$$

Acoustic phase lag through the electrode layer is determined using equation 2.8a in which $-Z_1T_1=Z_0T_0$. The electrode thickness can then be determined using the relation $$h_1 = -\frac{Z_1}{2\pi f_1 \rho_1} \arctan\left(\frac{Z_0 T_0}{Z_1}\right)$$

in which the intrinsic resonance frequency of the electrode is estimated using the formula $$fr_1 = \frac{Z_1}{2h_1\rho_1}.$$

The weight ($m_1$) of the crystal blank and electrode is then taken using an electromechanical microbalance (not shown).

After a sufficiently thick layer of a material with unknown acoustic impedance $Z_2$ and density $\rho_2$ has been deposited, the quartz crystal's fundamental resonant frequency is measured ($f_2$). The weight ($m_2$) of the crystal is taken again on a microbalance. The difference with that of the previous weight measurement indicates the mass of the deposited film (Δm). The radius of the spot size of the deposited film is also measured using a measuring microscope and the area of the deposited spot is determined by ($A=\pi r^2$). Using the mathematical equations (2.8a) and (2.10a), a nonlinear equation is set up, as is now described.

Acoustic phase lag information is then determined through each layer deposited, including the electrode and blank. First, the tangent of the acoustic phase lag through the quartz blank and the electrode are determined at $f_2$, wherein $$T_0 = \tan\left(\frac{\pi f_2}{f_q}\right) \text{ and } T_1 = \tan\left(\frac{\pi f_2}{fr_1}\right),$$

respectively.

Equation (2.8a) determines the thickness of the electrode and equation (2.10a) is used for solving for the unknown specific acoustic impedance of the new material. In that relation, $Z_0$ and $Z_1$ are the specific acoustic impedance of quartz and electrode material, respectively and $Z_2$ is the unknown specific acoustic impedance (or equivalent z-ratio) of the deposited film that is being solved for.

From equation (2.8a) and the measured frequency with the electrode only, the estimate for the thickness of the electrode is obtained as:

$$h_1 = -\frac{Z_1}{2\pi f_1 \rho_1} \arctan\left(\frac{Z_0}{Z_1}\tan\left(\frac{\pi f_1}{f_q}\right)\right) \text{ or} \quad (2.19)$$

$$h_1 = -\frac{Z_1}{2\pi f_1 \rho_1} \arctan\left(\frac{Z_0 T_0}{Z_1}\right)$$

The associated intrinsic resonant frequency of the electrode layer alone is defined as $$fr_1 = \frac{Z_1}{2h_1\rho_1} \quad (2.20)$$

Then the nonlinear equation to solve for the unknown specific acoustic impedance $Z_2$ is obtained by expanding equation (2.10a) into the following relation:

$$\tan\left(\frac{2\pi f_2}{Z_2}\frac{\Delta m}{A}\right) + \frac{1}{Z_2}\left(\frac{Z_0\tan\left(\frac{\pi f_2}{f_q}\right) + Z_1\tan\left(\frac{\pi f_2}{fr_1}\right)}{1 - \frac{Z_0}{Z_1}\tan\left(\frac{\pi f_2}{f_q}\right)\tan\left(\frac{\pi f_2}{fr_1}\right)}\right) = 0, \text{ or} \quad (2.21)$$

$$Z_2 T_2 + \frac{Z_0 T_0 + Z_1 T_1}{1 - \frac{Z_0}{Z_1} T_0 T_1} = 0$$

Iterative root solving techniques, such as Newton-Raphson, Bisection or others may then be employed to solve for the unknown parameter $Z_2$.

According to one example, the frequency of a quartz blank, $f_0$=6037100 Hz. The specific acoustic impedance of AT-cut quartz, $Z_0$=8765000 Kg/(m²-s), z-ratio=1.0. The electrode material is aluminum. The frequency of the quartz blank-electrode, $f_1$=6016350 Hz. The specific acoustic impedance of aluminum, $Z_1$=8115741 Kg/(m²-s), z-ratio=1.08. In this instance the material deposited is AlQ3, which is an OLED material. The frequency of quartz blank-electrode-thin film, $f_2$=5906587.5 Hz and the resulting calculated unknown specific impedance, $Z_2$=1488621 Kg/(m²-s), z-ratio=5.888.

The exact analytical solution nearly eliminates thickness errors when several layers of different materials are sequentially deposited on the same monitor quartz crystal. The technique also allows one to accurately determine the specific acoustic impedance of an unknown material.

It will be readily apparent that there are other modifications and variations that will be apparent from the foregoing discussion to one of skill as embodied in the following claims.

The invention claimed is:

1. A method of measuring the thickness of a deposited film on a piezoelectric crystal, said method comprising the steps of:
   a) determining the fundamental resonance frequency of a piezoelectric crystal blank;
   b) applying an electrode to said crystal blank;
   c) determining the fundamental resonance frequency of the composite blank and applied electrode;
   d) applying a first deposited layer of a material onto said crystal blank and electrode;
   e) determining the resonance frequency of the composite resonator comprising said blank, said electrode and said deposited layer;
   f) determining acoustic phase lag across each of the crystal blank, electrode and deposited layer as computed at said resonance frequency; and
   g) computing the thickness of said deposited layer from the phase lag information and density of said material.

2. A method as recited in claim 1, wherein said fundamental resonance frequency determining step for said crystal blank includes at least one of directly measuring said blank and providing a blank having a specific fundamental resonance frequency designed within a very narrow range.

3. A method as recited in claim 1, wherein the determining acoustic phase lag step comprises the further step of computing tangent functions of the phase lags across the crystal blank, electrode and deposited layer respectively.

4. A method as recited in claim 3, including the further step of computing arctangent functions of said phase lag information through the deposited layer to yield equivalent phase lag therethrough.

5. A method as recited in claim 1, including the additional step of computing the intrinsic resonance frequency of said deposited layer using said thickness determination.

6. A method as recited in claim 5, wherein the acoustic phase lag through any deposited layer onto said crystal blank and said electrode is determined by the relationship $$-Z_N T_N = \frac{\sum_{i=0}^{N-1} Z_i T_i - \sum_{i=0}^{N-1}\sum_{j>i}^{N-1}\sum_{k>j}^{N-1}\frac{Z_i Z_k}{Z_j}T_i T_j T_k + \sum_{i=0}^{N-1}\sum_{j>i}^{N-1}\sum_{k>j}^{N-1}\sum_{l>k}^{N-1}\sum_{m>l}^{N-1}\frac{Z_i Z_k Z_m}{Z_j Z_l}T_i T_j T_k T_l T_m - \ldots}{1 - \sum_{i=0}^{N-1}\sum_{j>i}^{N-1}\frac{Z_i}{Z_j}T_i T_j + \sum_{i=0}^{N-1}\sum_{j>i}^{N-1}\sum_{k>j}^{N-1}\sum_{l>k}^{N-1}\frac{Z_i Z_k}{Z_j Z_l}T_i T_j T_k T_l - \ldots} = K$$

in which Z is the specific acoustic impedance, T is the tangent function of acoustic phase lag of previously deposited layers and K is the composite parameter of acoustic phase lag through any previously deposited layers.

7. A method as recited in claim 6, wherein the thickness of any deposited layer onto said blank and said electrode is determined by the relationship $$h_N = \frac{Z_N}{2\pi f \rho_N}\arctan(K/Z_N)$$

in which $h_N$ is the thickness of the deposited layer, f is the fundamental frequency of the composite resonator defined by said blank, said electrode and said at least one deposited layer, K is the composite parameter of acoustic phase lag through any previously deposited layers, $\rho_N$ is the density of the deposited layer and $Z_N$ is the specific acoustic impedance of the deposited layer.

8. A method as recited in claim 7, wherein the intrinsic resonance frequency of any deposited layer onto said blank and electrode is determined by the relationship $$fr_i = \frac{Z_i}{2h_i \rho_i}$$

in which $fr_i$ is the intrinsic resonance frequency of the deposited layer, $Z_i$ is the specific acoustic impedance of the deposited layer, $h_i$ is the thickness of the deposited layer and $\rho_i$ is the density of the deposited layer.

9. A method as recited in claim 1, including the step of measuring said a first deposited thickness prior to completion of deposition, making at least one successive thickness calculation at a later time $\Delta t$ and then determining the deposition rate based on the differences in thickness over $\Delta t$.

10. A method as recited in claim 1, wherein said crystal blank is at least one of AT-cut, SC-cut, IT-cut and FC-cut.

11. A method as recited in claim 1, including the step of depositing at least one or more additional layers upon said first layer, and determining the thickness of said layer by repeating each of steps e)-g).

12. A method as recited in claim 11, wherein said additional layers and said first layer of deposited material are dissimilar materials.

13. The method as recited in claim 12, wherein the crystal blank is vibrating in thickness shear mode, including one of AT-cut, SC-cut, IT-cut and FC-cut.

14. A method for determining the specific acoustic impedance of an unknown material by thin film deposition on a piezoelectric crystal blank, said method comprising the steps of:
   providing a piezoelectric crystal blank having a specific acoustic impedance;
   determining the fundamental resonance frequency of said piezoelectric crystal blank;
   applying an electrode having a specific acoustic impedance and density to said crystal blank;
   measuring the fundamental resonance frequency of said crystal blank and applied electrode;
   computing acoustic phase lag information across said crystal blank and said applied electrode at said resonance frequency;
   determining the thickness of said electrode based on said computed acoustic phase lag information and the density of said electrode;
   determining the mass of said crystal blank and said applied electrode;
   depositing a layer of material having unknown acoustic impedance and unknown density onto said previously applied electrode and crystal blank;
   measuring the fundamental resonant frequency of said composite resonator comprising said crystal blank, said electrode and said deposited layer;
   weighing said crystal blank, said applied electrode and said deposited layer;
   determining the mass of said deposited layer based on said weight measurements;
   determining the area of the deposited layer on said crystal blank;
   estimating the thickness of said deposited layer based on the determined mass and area measurements;
   computing acoustic phase lag information across the crystal blank, said electrode and said deposited layer at said measured resonant frequency; and
   determining the specific acoustic impedance of said deposited film layer based upon said phase lag information and said thickness measurement.

15. The method as recited in claim 14, wherein said fundamental resonance frequency determining step for said crystal blank includes at least one of directly measuring said blank and providing a blank having a specific fundamental resonance frequency designed within a very narrow range.

16. The method as recited in claim 14, wherein said specific acoustic impedance determining step includes the additional step of constructing a non-linear equation including said acoustic phase lag information and the determined layer thickness.

17. The method as recited in claim 16, wherein said constructed non-linear equation is $$Z_2 T_2 + \frac{Z_0 T_0 + Z_1 T_1}{1 - \frac{Z_0}{Z_1} T_0 T_1} = 0,$$

in which $Z_2$ is the specific acoustic impedance of the deposited layer, $T_2$ is the tangent function of the acoustic phase lag of the deposited layer, $Z_1$ is the specific acoustic impedance of the electrode, $T_1$ is the tangent function of the acoustic phase lag of the electrode, $Z_0$ is the specific acoustic impedance of the crystal blank and $T_0$ is the tangent function of the acoustic phase lag of the crystal blank, respectively.

* * * * *